US011155826B2

(12) United States Patent
Mitsuhara et al.

(10) Patent No.: US 11,155,826 B2
(45) Date of Patent: Oct. 26, 2021

(54) METHOD FOR PRODUCING GENOME EDITED PLANT

(71) Applicant: National Agriculture and Food Research Organization, Tsukuba (JP)

(72) Inventors: Ichiro Mitsuhara, Tsukuba (JP); Yuki Yanagawa, Tsukuba (JP); Kasumi Yamada, Tsukuba (JP); Seiichi Toki, Tsukuba (JP); Ayako Yokoi, Tsukuba (JP)

(73) Assignee: National Agriculture and Food Research Organization, Tsukuba (JP)

( * ) Notice: Subject to any disclaimer, the term of this patent is extended or adjusted under 35 U.S.C. 154(b) by 52 days.

(21) Appl. No.: 16/473,856

(22) PCT Filed: Dec. 25, 2017

(86) PCT No.: PCT/JP2017/046368
§ 371 (c)(1),
(2) Date: Jun. 26, 2019

(87) PCT Pub. No.: WO2018/123938
PCT Pub. Date: Jul. 5, 2018

(65) Prior Publication Data
US 2020/0283781 A1 Sep. 10, 2020

(30) Foreign Application Priority Data
Dec. 27, 2016 (JP) .............................. JP2016-253306

(51) Int. Cl.
*C12N 15/82* (2006.01)
*C12N 5/04* (2006.01)

(52) U.S. Cl.
CPC ........... *C12N 15/8205* (2013.01); *C12N 5/04* (2013.01)

(58) Field of Classification Search
CPC .................................................. C12N 15/8205
See application file for complete search history.

(56) References Cited

U.S. PATENT DOCUMENTS

2011/0145940 A1    6/2011    Voytas et al.

FOREIGN PATENT DOCUMENTS

JP        2013-513389 A      4/2013

OTHER PUBLICATIONS

Gallois, P. and Marinho, P. in Methods in Molecular Biology, 1995 vol. 49. Plant Gene Transfer and Expression Protocols Edited by H. Jones; Humana Press Inc., Totowa N.J. pp. 39-48. (Year: 1995).*
Tampakaki, A. P., Fronteirs in Plant Science (Mar. 2014) vol. 5, No. 114, pp. 1-19. (Year: 2014).*
Lacroix, B. and Citovsky, V., PLoS Pathog; (Mar. 11, 2016) 12(3); pp. 1-15. (Year: 2016).*
Tampakaki, A. P., Frontiers in Plant Science (Mar. 2014) vol. 5, No. 114, pp. 1-19. (Year: 2014).*
Guy R. Cornelis, et al., "Assembly and Function of Type III Secretory Systems", Annu. Rev. Microbiol., 2000, pp. 735-774, vol. 54.
Lisa M. Schechter, et al., "*Pseudomonas syringae* Type III Secretion System Targeting Signals and Novel Effectors Studied with a Cya Translocation Reporter", Journal of Bacteriology, Jan. 2004, pp. 543-555, vol. 186, No. 2.
Takufumi Mukaihara, et al., "Genome-Wide Identification of a Large Repertoire of *Ralstonia solanacearum* Type III Effector Proteins by a New Functional Screen", MPMI, 2010, pp. 251-262, vol. 23., No. 3.
Ayako Furutani, et al., "Identification of Novel Type III Secretion Effectors in *Xanthomonas oryzae* pv. *oryzae*", MPMI, 2009, pp. 96-106, vol. 22. No. 1.
Daniel F. Voytas, et al., "Plant Genome Engineering with Sequence-Specific Nucleases", Ann. Rev. Plant Biol., 2013, pp. 327-350, vol. 64.
Erin L. Doyle, et al., "TAL effectors: highly adaptable phytobacterial virulence factors and readily engineered DNA targeting proteins", Trends Cell Biol., Aug. 2003, pp. 390-398, vol. 23, No. 8.
Masaki Endo, et al., "Targeted Mutagenesis in Rice Using TALENs and the CRISPR/Cas9 System", Methods in Molecular Biology, 2016, pp. 123-135, vol. 1469.
Je Wook Woo, et al., "DNA-free genome editing in plants with preassembled CRISPR-Cas9 ribonucleoproteins", Nature Biotechnology, Nov. 2015, pp. 1161-1164, vol. 33, No. 11.
Saminathan Subburaj, et al., "Site-directed mutagenesis in *Petunia* X *hybrida* protoplast system using direct delivery of purified recombinant Cas9 ribonucleoproteins", Plant Cell Rep., 2016, pp. 1535-1544, vol. 35.
Sergei Svitashev, et al., "Genome editing in maize directed by CRISPR-Cas9 ribonucleoprotein complexes", Nature Communications, Nov. 16, 2016, 7 pages, vol. 7, No. 13274.
Zahir Ali, et al., "Efficient Virus-Mediated Genome Editing in Plants Using the CRISPR/Cas9 System", Molecular Plant, Aug. 2015, pp. 1288-1294, vol. 8.

(Continued)

*Primary Examiner* — Russell Kallis
(74) *Attorney, Agent, or Firm* — Sughrue Mion, PLLC

(57) ABSTRACT

The present inventors found that the efficiency of introducing a protein into a plant dramatically increases as compared with conventional methods for cultivating a bacteria-infected plant as it is when the protein of interest is expressed with bacteria having the type III secretion system, the bacteria are brought into contact with the plant, and then the infected tissues are cultured under bacteriostatic conditions for a certain period of time.

3 Claims, 12 Drawing Sheets
Specification includes a Sequence Listing.

(56) References Cited

OTHER PUBLICATIONS

Kiaw Kiaw Ng, et al., "Intracellular Delivery of Proteins via Fusion Peptides in Intact Plants", PLOS One, Apr. 21, 2016, 19 pages, vol. 10.

Daniela Buttner, et al., "Protein Export According to Schedule: Architecture, Assembly, and Regulation of Type III Secretion Systems from Plant- and Animal-Pathogenic Bacteria", Microbiology and Molecular Biology Reviews, Jun. 2012, pp. 262-310, vol. 76, No. 2.

International Search Report for PCT/JP2017/046368 dated Mar. 20, 2018 [PCT/ISA/210].

International Preliminary Report on Patentability dated Jul. 11, 2019 in PCT/JP2017/046368.

* cited by examiner

METHOD FOR PRODUCING GENOME EDITED PLANT

CROSS REFERENCE TO RELATED APPLICATIONS

This application is a National Stage of International Application No. PCT/JP2017/046368, filed on Dec. 25, 2017, which claims priority from Japanese Patent Application No. 2016-253306, filed on Dec. 27, 2016.

TECHNICAL FIELD

The present invention relates to a method for producing a genome edited plant using a bacterial type TI secretion system.

BACKGROUND ART

Genome editing technology is a technique of preparing new cells and varieties by introducing a mutation to a target site of a specific gene to modify the activity of the encoded protein (for example, substitution from active form to inactive form or substitution from inactive form to active form). This technique differs from conventional genetic recombination techniques in that it simply introduces a mutation to an endogenous gene, thereby making it possible to create varieties and strains which do not carry foreign genes (NPL 1).

Genome editing technology generally uses a nuclease imparted with a site specificity (nucleic acid (DNA) cleaving enzyme) in order to give two characteristics of site specificity on the genome and modification of the genome. As such a nuclease, development has been conducted one after another since 2005 on first generation ZFNs (Zinc Finger Nucleases) and following second generation and third generation genome editing techniques dealing with TALENs (Transcription Activator Like Effector Nucleases), CRISPR-Cas9 (Clustered Regularly Interspaced Short Palindromic Repeats CRISPR-Associated Proteins 9), and the like (NPL 2). For the purpose of imparting a nuclease with a site specificity, sequence recognition domains which bind to the target DNA (ZF domains, TALE domains) are used in ZFNs and TALENs, and RNA having a sequence complementary to the target DNA (guide RNA) is used in CRISPR/Cas9.

In the case of utilizing an artificial nuclease for genome editing including TALENs for crop breeding, the mainstream method for plants is to introduce an artificial nuclease gene by a genetic recombination technique such as the *Agrobacterium* method (NPL 3). However, since the *Agrobacterium* method incorporates an artificial nuclease gene into genomic DNA of the target plant, it is necessary to remove the unnecessary artificial nuclease gene after introducing a modification to the target gene of the plant. In such a case, the gene of a protein for genome editing can be removed in plants capable of crossing, but there are many crops which are virtually incapable of removing unnecessary genes by crossing, such as vegetative propagation plants and woody plants.

In such circumstances, development has also been conducted for plants on a technique of introducing an artificial nuclease as a protein directly into a cell to perform genome editing without incorporation of a gene into the genome. However, plant species for application are limited due to, for example, the need for protoplasting (NPLs 4 and 5). Similarly, there is also a report of successful target mutation by directly introducing RNP (CRISPR/Cas9 protein RNA complex) into a corn embryo with a particle gun (NPL 6). However, since plants capable of individual regeneration are limited even in ordinary genetic recombination, the method using a particle gun is considered to be more difficult for genome editing. Meanwhile, there is also an attempt to conduct genome editing of plants by virus mediation (NPL 7), but there is no known example of successful genome editing by introducing a genome editing protein using a virus due to, for example, restrictions on the length of foreign genes which can be introduced into viruses. In addition, in the case of using a recombinant virus, there is also an obstacle such as the difficulty in proving the absence of virus in the plant after genome editing. Another known method for introducing a protein into a plant cell is, for example, a method using a transmembrane peptide (NPL 8), but there is no report of application to plant genome editing.

Here, the function of the type III secretion system is considered such that pathogenic bacteria introduce a special protein into host cells to disturb the functions of the host cells and facilitate parasitism, and some Gram negative bacteria are known to have this function (NPL 9). Additionally, methods have been reported of introducing foreign proteins into plant cells using this system (NPLs 10 to 12). However, there is no report of successful production of redifferentiated individuals derived from cells into which foreign proteins are introduced, including artificial nucleases.

CITATION LIST

Non Patent Literature

[NPL 1] Voytas, Annu. Rev. Plant Biol. 64: 327-350 (2013)
[NPL 2] Doyle et al., Trends Cell Biol 23: 390-398 (2013)
[NPL 3] Endo et al., Methods in Molecular Biology Volume 1469 pp 123-135 (2016)
[NPL 4] Woo et al., Nature Biotech. 33: 1162-1164 (2016)
[NPL 5] Subburaj et al., Plant Cell Rep. 35: 1535-1544 (2016)
[NPL 6] Svitashev et al., Nature Communication 7: 13274 (2016)
[NPL 7] Ali et al., Molecular Plant 8: 1288-1291 (2015)
[NPL 8] Ng et al., Plos One 10: 1371 (2016)
[NPL 9] Buttner, Mocrbiology and Molecular Biology 76: 262-310 (2012)
[NPL 10] Schechter et al., J Bacteriol, 186: 543-555 (2004)
[NPL 11] Mukaihara et al., MPMI 23: 251-262 (2010)
[NPL 12] Furutani et al., MPMI 2: 96-106 (2009)

SUMMARY OF INVENTION

Technical Problem

For the purpose of producing a plant into which a foreign protein has been introduced using the type III secretion system possessed by bacteria, the present inventors used TALENs, an artificial enzyme for genome editing, as an example of a foreign protein to perform cultivation by infecting tobacco leaves with bacteria in which TALENs was expressed by the above-described conventional method. However, it was found that, due to the introduction of TALENs, the frequency of obtaining plant tissues with target gene mutation was low and unstable.

The present invention has been made in view of the above problem, and an object thereof is to provide a method capable of efficiently producing a plant into which a desired protein has been introduced using the type III secretion system possessed by bacteria.

Solution to Problem

The present inventors have made earnest studies to achieve the above object and found as a result that the efficiency of introducing a protein into a plant dramatically increases as compared with conventional methods for cultivating a bacteria-infected plant as it is when the protein of interest is expressed with bacteria having the type III secretion system, the bacteria are brought into contact with the plant, and then the infected tissues are cultured under bacteriostatic conditions for a certain period of time. This finding has led to the completion of the present invention.

Specifically, the present invention is a method for producing a plant into which the protein of interest has been introduced using bacteria having the type III secretion system, the method including co-culturing the bacteria and the plant tissues under bacteriostatic conditions for a certain period of time. More specifically, the present invention provides the following.

[1] A method for producing a plant into which a desired protein is introduced, the method comprising the steps of (a) to (d):
(a) preparing transformed bacteria by introducing DNA encoding a desired protein into a bacteria having a type III secretion system;
(b) bringing the transformed bacteria into contact with a plant;
(c) transferring a tissue of the plant infected with the transformed bacteria to a medium, followed by culture under a condition that the transformed bacteria are suppressed from proliferating but not killed; and
(d) redifferentiating the tissue of the plant by performing culture under a condition that the transformed bacteria are killed.

[2] The method according to [1], wherein
the culturing condition of the step (c) is at least one of limitation on a nutrient source and addition of an antibiotic.

[3] The method according to [1] or [2], wherein
a period of the culture of the step (c) is one to ten days.

Advantageous Effects of Invention

The present invention makes it possible to efficiently produce a plant into which the protein of interest has been introduced. In a plant produced by the method of the present invention, a gene encoding the protein of interest is not incorporated into the plant genome. For this reason, it is unnecessary to remove the gene after the protein of interest is no longer needed. This is also advantageous in terms of safety in the case of using the plant as food and environment (biodiversity) in the case of cultivation in the outside, for example.

BRIEF DESCRIPTION OF DRAWINGS

FIG. 2B provides photos illustrating the results of detecting the occurrence of genome editing in the leaf pieces using luciferase activity as an index after three days of culture.

FIG. 2C provides photos illustrating the results of detecting the occurrence of genome editing using luciferase activity as an index (a) as of one month from inoculation, (b) when rooted individuals were obtained in the rooting medium, and (c) when mutated individuals were obtained after transferring the rooted individuals to a pot.

FIG. 3 provides photos illustrating the results of detecting the occurrence of genome editing in the leaf pieces using luciferase activity as an index one day, three days, and five days after culture.

FIG. 4 provides photos illustrating the results of detecting the occurrence of genome editing in the leaf pieces using luciferase activity as an index one day, two days, five days, and six days after culture.

FIG. 5 provides photos illustrating the results of detecting the occurrence of genome editing in the leaf pieces using luciferase activity as an index three days after culture.

FIG. 6 provides photos illustrating the results of detecting the occurrence of genome editing in the leaf pieces using luciferase activity as an index three days after culture.

FIG. 8B provides photos illustrating the results of detecting the occurrence of genome editing using hygromycin resistance as an index in the seventh week after inoculation.

FIG. 9 provides photos illustrating the results of detecting the occurrence of genome editing using luciferase activity as an index when mutated individuals were obtained after transferring the rooted individuals to a pot. Following the 1st ATG (left rectangles) in the sequence, there is an I-SceI recognition sequence (right rectangle).

DESCRIPTION OF EMBODIMENTS

Figure 1:
FIG. 1 is a diagram illustrating the construction of the vector "pBI121-sGFP-wTALEN-ELUC" used in Present Examples.

A method of the present invention including producing a plant into which a desired protein is introduced prepares transformed bacteria by first introducing DNA encoding the desired protein into bacteria having the type III secretion system (step (a)).

The "type III secretion system" in the present invention is a protein secretion system conserved in Gram-negative bacteria, and serves to directly inject the protein produced by itself into the host. The "bacteria having the type III secretion system" used in the present invention are not particularly limited as long as they use a plant as a host, and examples thereof include phytopathogenic bacteria such as *Xanthomonas* genus bacteria, *Pseudomonas* genus bacteria, *Ralstonia* genus bacteria, and *Erwinia* genus bacteria as well as symbiotic bacteria such as *rhizobia*. Examples of the *Xanthomonas* genus bacteria include *Xanthomonas oryzae* and pathovars (pv.) of *Xanthomonas campestris* including *Xanthomonas campestris* pv. *campestris* (Xcc) used in the present invention, examples of the *Pseudomonas* genus bacteria include pathovars of *Pseudomonas syringae*, examples of the *Ralstonia* genus bacteria include *Ralstonia solanacearum*, and examples of the *Erwinia* genus bacteria include *Erwinia carotovora*.

The "desired protein" in the present invention is not particularly limited. In the present invention, it is possible to use any protein desired to be introduced into a plant. For the purpose of genome editing, examples of the desired protein include fusion proteins such as ZFNs (U.S. Pat. Nos. 6,265, 196, 8,524,500, and 7,888,121 and European Patent No. 1720995), TALENs (U.S. Pat. Nos. 8,470,973 and 8,586, 363), and PPR fused with nuclease domain (pentatricopeptide repeat) (Nakamura et al., Plant Cell Physiol 53: 1171-1179 (2012)). In addition, examples include nucleases used in CRISPR-Cas9 (U.S. Pat. No. 8,697,359 and International Publication No. WO2013/176772), CRISPR-Cpf1 (Zetsche B. et al., Cell, 163 (3): 759-71, (2015)), and the like. The nuclease domains of the fusion proteins described above can be substituted with different modification enzyme domains depending on the purpose. Examples of the different modification enzyme domains include transcription activator domains, transcription repressor domains, deaminase domains, DNA methylation enzyme domains, histone modification enzyme domains (acetylation, deacetylation, methylation, demethylation, and the like), and recombinase domains.

In addition to genetic modification by genome editing molecules, it is also possible to perform, for example, induction of flowering by florigen and promotion of dedifferentiation by introduction of a reprogramming factor (improvement of transformation efficiency). In addition, one may think of improving the efficiency of mutation introduction by introducing a dominant negative type protein of DNA repair related factor together with genome editing molecules.

The "desired protein" in the present invention may be degraded once it is introduced into a plant and its purpose is achieved.

DNA encoding the desired protein is usually inserted into a vector appropriate for the expression in the bacteria and then introduced by the bacteria. Examples of the vector usable include pME6031 having the VS1 replication origin (Heeb et al. MPMI 13: 232-237 (2000)) and pHM1 derived from pRI40 (GenBank accession number of EF059993). In addition, examples usable include broad host range vectors such as pDSK519 (GenBank accession number of JQ173098, Keen et al., Gene 70: 191-197 (1988)). These plasmids can be introduced into bacteria by known methods such as the electroporation method.

In addition, in the present invention, it is also possible to use a method for introducing a gene to a bacterial genome using a transposon or a viral vector. Consider the case of incorporating a gene encoding the protein of interest into a transposon contained in a plasmid such as pBSL118 (Tn5) (Alexeyev et al. Can J. Microbiol 41: 1053-1055 (1995)) or pME3280 (Tn7) (Zuber et al. MPMI 16: 6354-644 (2003)). Then, it is possible to transfer the transposon containing that gene to a bacterial genome.

The method of the present invention next brings the transformed bacteria into contact with the plant (step (b)).

The "plant" as a target for contact with the transformed bacteria prepared in step (a) is not particularly limited as long as it is a plant into which bacteria having the type III secretion system can introduce a protein using the system. Examples of the plant to be brought into contact with the *Xanthomonas* genus bacteria include, but are not limited to, Brassicaceae plants such as thale cress, Japanese radish, rapeseed, and cabbage, Gramineae plants such as rice, wheat, and corn, Solanaceae plants such as tobacco, eggplant, and tomato, Leguminosae plants such as soybean, adzuki bean, and broad bean, Cucurbitaceae plants such as cucumber, watermelon, and melon, and Rosaceae plants such as apple, rose, and pear, examples of the plant to be brought into contact with the *Pseudomonas* genus bacteria include, but are not limited to, Brassicaceae plants such as thale cress, Japanese radish, rapeseed, and cabbage, Gramineae plants such as rice, wheat, and corn, Solanaceae plants such as tobacco, eggplant, and tomato, Leguminosae plants such as soybean, adzuki bean, and broad bean, Cucurbitaceae plants such as cucumber, watermelon, and melon, Rosaceae plants such as apple, rose, and pear, Oleaceae plants such as olive, sweet osmanthus, jasmine, and lilac, and Asteraceae plants such as *chrysanthemum*, lettuce, and artichoke, examples of the plant to be brought into contact with the *Ralstonia* genus bacteria include, but are not limited to, Solanaceae plants such as tobacco, eggplant, tomato, and potato, Leguminosae plants such as soybean, adzuki bean, and broad bean, Rosaceae plants such as apple, rose, and pear, Zingiberaceae plants such as ginger, turmeric, and Japanese ginger, Musaceae plants such as Japanese banana, banana, and abaca, and Oleaceae plants such as olive, sweet osmanthus, jasmine, and lilac, examples of the plant to be brought into contact with the *Erwinia* genus bacteria include, but are not limited to, Brassicaceae plants such as thale cress, Japanese radish, rapeseed, and cabbage, Solanaceae plants such as tobacco, eggplant, tomato, and potato, Rosaceae plants such as apple, rose, and pear, Gramineae plants such as rice, wheat, and corn, and Asteraceae plants such as *chrysanthemum*, lettuce, and artichoke, and examples of the plant to be brought into contact with the *rhizobia* include, but are not limited to, Leguminosae plants such as soybean, adzuki bean, and broad bean. For example, the CyaA assay method (Furutani et al., MPMI 22: 96-106 (2009), Mukaihara et al., Molecular Microbiology 54: 863-875 (2004)) can be used to select a combination of plant and bacteria suitable for the present invention and a signal sequence for transporting the desired protein to the type III secretion system.

As a method for bringing the transformed bacteria into "contact" with the plant, it is possible to use, for example, a known pathological method such as the infiltration (immersion) method including injection of a bacterial solution into an intercellular space, the pruned leaf inoculation method including cutting of the leaf tip with scissors soaked in a bacterial solution, the spray method including spraying of a bacterial solution, or the leaf disc method including soaking of cut leaves in a bacterial solution. The transformed bacteria do not need to be brought into contact with the whole plant, but may be brought into contact with part of the plant, for example a specific tissue on the plant or a specific tissue isolated from the plant. Examples of the specific tissue include leaves, stems, shoot apices (growing points), roots, tubers, and calluses.

The method of the present invention next transfers a tissue of the plant infected with the transformed bacteria to a medium, followed by culture under a condition that the transformed bacteria are suppressed from proliferating but not killed (specifically, under bacteriostatic conditions) (step (c)).

The present inventors found that it is impossible to efficiently produce a plant into which the desired protein has been introduced due to the proliferation of transformed bacteria in the case of culture under normal plant tissue culturing conditions and due to the death of transformed bacteria in the case of culture under bactericidal conditions. In light of the above, the present invention co-cultures the bacteria and the plant tissue under bacteriostatic conditions to introduce the protein of interest from the bacteria to the plant tissue.

As the "medium" for culturing the tissue of a plant infected with transformed bacteria, it is possible to use a common medium used for culturing plant tissues. Examples of such a medium include MS medium (Murashige and Skoog, Physiol. Plant, 18: 100-127 (1962)), LS medium (Linsmaier and Skoog, Physiol. Plant. 18: 100-127 (1965)), Gamborg B5 medium (Gamnorg et al., Exp. Cell. Res. 50: 151-158 (1968)), N6 medium (Chu, Science press, Beijing pp. 43-50 (1978)), KNUDSON C medium (Knudson, Am. Orchid Soc. Bull., 15: 214-217 (1946)), R2 medium (Ohira et al., Plant and Cell Physiology 14: 1113 (1973)), Tuleeke medium (Tuleeke and Nickell, Science 130: 863-864 (1959)), and White's medium (White, A handbook of plnt tissue culture, pp 103, Cattell, Lancaster, Pa. (1963)).

As the "condition that the transformed bacteria are suppressed from proliferating but not killed" in the culture of the present step, its examples include limitation on the nutrient source in the medium (such as a carbon source or a nitrogen source), addition of an antibiotic to the medium at a bacteriostatic concentration, and change of the temperature condition.

In the case of limiting the nutrient source, examples of the carbon source include sucrose, and examples of the nitrogen source include nitrates, ammonium salts, and amino acids. The limitation is, for example, no addition or reduction in amount added to the medium. In addition, in the case of adding an antibiotic, examples of a preferred antibiotic include, but are not limited to, bacteriostatic antibiotics including cephem-based antibiotics such as Cefotax (cefotaxime), penicillin-based antibiotics such as carbenicillin, tetracycline-based antibiotics such as tetracycline, cell wall synthesis inhibition types such as cycloserine, chioramphenicol-based antibiotics such as chloramphenicol, and macrolide-based antibiotics such as azithromycin. In addition, one may think of bacteriostatically using even an antibiotic generally considered bactericidal as described later under the conditions of a concentration reduced to the extent that does not kill the transformed bacteria. The concentration of antibiotic added is, although it depends on the type, usually 1 to 1000 µg/ml and preferably 2 to 250 µg/ml. For example, in the case of using Cefotax (cefotaxime) as an antibiotic, the concentration is particularly preferably 100 to 250 µg/ml. In addition, as the condition in the case of changing the temperature condition, it is possible to employ, for example, a temperature condition lower by two to seven degrees than the normal temperature condition applied to plant species for tissue culture. For example, while tobacco, tomato, and the like are usually cultured at 25 to 28 degrees, the present invention may set the temperature to 18 to 24 degrees. In the present invention, those conditions may be used in combination. For example, it is also possible to add an antibiotic while limiting the nutrient source.

The condition that the transformed bacteria are suppressed from proliferating but not killed is preferably the addition of an antibiotic to the medium. In the case of adding an antibiotic to suppress the proliferation of transformed bacteria, the nutrient source such as sucrose does not necessarily have to be limited. This makes it possible to suppress the proliferation of transformed bacteria while preventing damage to the cultured tissue.

It is possible to evaluate whether or not a certain culturing condition is a condition which suppresses the proliferation of transformed bacteria based on whether or not the proliferation of the transformed bacteria is suppressed as compared with the case of culture under a normal culturing condition, for example in a callus • regeneration induction medium containing sucrose without the addition of Cefotax [1× Murashige and Skoog (MS), 1× MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of α-naphthaleneacetic acid, 1 µg/ml of 6-benzylaminopurine, 30 g/L of sucrose, 8.5 g/L of agar, and pH of 5.8]. For example, consider the case of homogenizing transformed bacteria cultured under various conditions and then measuring the number of bacteria by plate culture method or the like. When the number of bacteria under a certain culturing condition is smaller than the number of bacteria under a normal culturing condition (when the decrease in the number of bacteria is, for example, 10% or more, 20% or more, 30% or more, 40% or more, 50% or more, 60% or more, 70% or more, 80% or more, 90% or more, 95% or more, or 99% or more), it is possible to evaluate that the proliferation of transformed bacteria is suppressed. Here, the "suppression of proliferation" includes complete suppression of proliferation (stopping of proliferation).

In addition, it is possible to evaluate whether or not a certain culturing condition is a condition which kills transformed bacteria based on whether or not the proliferation of transformed bacteria is observed in the case of culture under that culturing condition followed by culture under a normal culturing condition. If the transformants proliferate after transitioning to the normal culturing condition, it is possible to evaluate that the transformants are not killed. Meanwhile, if the transformants do not proliferate, it is possible to evaluate that the transformants are killed. For example, the proliferation of transformed bacteria may be evaluated by measuring the number of bacteria for the transformed bacteria as described above, or may be evaluated by white turbidity around the leaf pieces.

The culturing period in the present step is not limited as long as it is a period sufficient for introducing a protein into a plant, and is usually one to ten days. The culturing period is preferably one to four days without the addition of sucrose. It is possible to apply general conditions for the culture of plant tissues except for the restricted conditions.

The method of the present invention next performs culture under a condition that the transformed bacteria are killed (under bactericidal conditions) to redifferentiate the tissue of the plant (step (d)).

As the "medium" in the culture of the present step, it is possible to use a common medium used for culturing plant tissues, as described above. As the "condition that the transformed bacteria are killed," it examples include addition of an antibiotic to the medium at a lethal concentration. Preferred examples of the antibiotic include, but are not limited to, bactericidal antibiotics including aminoglycoside-based antibiotics such as kanamycin, rifamycin-based antibiotics such as rifampicin, carbapenem-based antibiotics such as imipenem, polypeptide-based antibiotics such as polymyxins, fosfomycin-based antibiotics such as fosfomycin, new quinolone-based antibiotics such as nadifloxacin, R-lactam-based antibiotics such as penicillins, and pyridone carboxylic acid-based antibiotics such as nalidixic acid. In addition, one may think of using even an antibiotic generally considered bacteriostatic as described above under the conditions of a concentration increased to the extent that kills the transformed bacteria. The concentration of antibiotic added is usually 1 to 1000 µg/ml and preferably 2 to 250 µg/ml.

Once the transformed bacteria are killed, then culture is not necessarily needed under the condition that the transformed bacteria are killed. Thus, the "performing culture under a condition that the transformed bacteria are killed" in the present step is not meant to require culture under that condition in the entire period for the process of redifferentiating the plant tissue. The culturing period under the condition that the transformed bacteria are killed is usually two days to two months and preferably one week to four weeks after step (a).

As a method for redifferentiating a plant tissue by tissue culture to obtain an individual, it is possible to use a method established in the present technical field (Protocols for Plant Transformation, edited by Yutaka Tabei, Kagaku Dojin Publishing, pp. 340-347 (2012)).

Consider the case where a mutation has been introduced using genome editing molecules as the protein of interest, and a plant tissue of a marginal chimera or a sectorial chimera (or marginal sectorial chimera) is obtained. It is possible to eliminate the chimera state by continuously removing side shoots with a high percentage of cells carrying the mutation of interest (Shozo Kobayashi, Shimpen Kaju Engei Gaku III, Breeding and Varieties 4) Other Breeding Methods p. 68-69 (2002), The Chemical Daily Co., Ltd., Aida et al., Plant Biotech 33: 45-49 (2016)). In addition, as a method for obtaining a homozygous individual into which the mutation of interest has been introduced, it is possible to use, for example, the literature (M. Endo et al., Chromosome and Genomic Engineering in Plants, Volume 1469 of the series Methods in Molecular Biology, pp 123-135 (2016)). It is also possible by crossing to obtain a homozygous individual in accordance with the Mendelian inheritance rules.

EXAMPLES

Hereinafter, the present invention is more specifically described based on Examples, but the present invention is not limited to Examples.

(Example 1) Construction of Reporter Gene

A special reporter gene was constructed to make it possible to detect, using a visible marker gene, the possibility of introducing a mutation by a genome editing enzyme into plant cells (FIG. 1). The reporter gene is transcribed with the coding regions (ORF) of the green fluorescent protein (sGFP) and the luciferase gene (ELUC) under the control of a high expression promoter common in plants. Here, the coding region of sGFP is present in front of the transcription region (5' side of mRNA), and a spacer region is followed by the ELUC coding region. The spacer region is inserted with a fragment of the partially modified rice Waxy gene, and the reading frames for the coding region of the GFP gene and the coding region of the ELUC gene are arranged so as to be different from each other. In eukaryotes, with some exceptions, the translation from mRNA to protein starts from the first start codon (1st ATG) on the 5' side of mRNA and stops when reaching the stop codon (nonsense codon). In the construction product prepared this time, the stop codon appears at the spacer sequence part. For this reason, the translation from mRNA transcribed from the present construction product stops when the sGFP gene part is translated and does not express the ELUC gene.

When a genome editing enzyme which recognizes the spacer part functions to produce a cleavage in that part, the cleavage is repaired by the intracellular DNA repair mechanism. Here, a mutation such as deletion or insertion of a base is introduced at a certain frequency. In the case of repair without mutation introduction, the site is again the target of a genome editing enzyme, which results in frequent introduction of mutation. When a deletion or insertion mutation is introduced into the spacer part, a fusion gene in which the reading frames (frames) of the sGFP gene and the ELUC gene coincide with each other with a probability of ⅓ is created. In this case, mRNA transcribed from the fusion gene into which a mutation has been introduced (in which genome editing has occurred) has a sequence of sGFP-Wx spacer-ELUC, and translates the sequence as a series of peptide chains. Therefore, one-third of the cells in which genome editing has occurred acquire a luminescence ability by the addition of luciferin, the substrate of the luciferase gene.

As described above, a plant inserted with the special reporter gene of Present Example is a reporter plant which can detect the occurrence of genome editing targeting the Wx spacer sequence using luminescence as an index.

The sequence encoding ELUC was amplified by the PCR method from pELUC-test (TOYOBO) using primers EcoRI-ELUC-F and SpeI-ELUC-R (SEQ ID NOs: 3 and 4). The plasmid obtained by cloning the PCR product using the Zero blunt TOPO PCR cloning kit was named "Zero-ELUC." This Zero-ELUC was treated with EcoRI and SpeI to excise the ELUC sequence, followed by insertion of the obtained DNA fragments into pE12Ω-MCS treated with EcoRI and SpeI in the same manner to prepare "pE12Ω-ELUC." A TALENs gene which recognizes and cuts the Wx sequence with high efficiency has already been produced by Yokoi et al. (Nishizawa-Yokoi et al., Plant Physiol. 170: 653-666 (2016)). DNA sequence "wTALEN" fragments containing Wx gene fragments recognized by the TALENs were prepared by annealing (pairing) two single-stranded DNAs "XbaI-wTALEN-EcoRI-F" and "EcoRI-wTALEN-XbaI-R" (SEQ ID NOs: 1 and 2). The pE120-ELUC was treated with XbaI and EcoRI, and the wTALEN fragments were inserted into the XbaI and EcoRI sites to prepare "pE120-wTALEN ELUC." This pE12 Ω-wTALEN-ELUC was treated with XbaI and SacI, and the obtained DNA fragments containing wTALEN-ELUC were inserted into a pBI121 vector treated with XBI and SacI to prepare "pBI121-wTALEN-ELUC." The sequence encoding sGFP was amplified by the PCR method using primers XbaI-sGFP-F and XbaI-sGFP-R (SEQ ID NOs: 5 and 6), treated with XbaI, and inserted into pBI121-wTALEN-ELUC treated with XbaI in the same manner to produce pBI121-sGFP-wTALEN-ELUC.

TABLE 1

| Name | Sequence (5' → 3') |
|---|---|
| XbaI-wTALEN-EcoRI-F | CTAGAATGGTCCTTATAAGCACATATC GCATGGTACCATATATGTTTGAGTTTT AGCGACG (SEQ ID NO: 1) |
| EcoRI-wTALEN-XbaI-R | AATTCGTCGCTAAAACTCAAACATATA TGGTACCATGCGATATGTGCTTATAAG GACCATT (SEQ ID NO: 2) |
| EcoRI-ELUC-F | TGAATTCATGGAGAGAGAGAAGAACGT G (SEQ ID NO: 3) |
| SpeI-ELUC-R | TACTAGTTTACAGCTTAGAAGCCTTCT CC (SEQ ID NO: 4) |
| XbaI-sGFP-F | AGTCTAGAATGGTGAGCAAGGGCGAGG (SEQ ID NO: 5) |
| XbaI-sGFP-R | AGTCTAGACTTGTACAGCTCGTCCATG C (SEQ ID NO: 6) |

The prepared pBI121-sGFP-wTALEN-ELUC was introduced into a tobacco plant (*Nicotiana tabacum* cv. Samsun NN) using *Agrobacterium* (LBA4404) as an intermediate host. A second generation individual introduced with sGFP-wTALEN-ELUC was used for the experiment. The tobacco plant was grown in a culture room with a modulated temperature of 25° C. and modulated light of 16-hour light period/8-hour dark period.

(Example 2) Construction of TALENs Gene

A TAL effector repeated sequence was constructed by the Golden Gate assembly method (Cermak et al., Nucl. Acids. Res. 39, e82 (2011)). The repeating of Wx_TALEN-A1 was constructed by joining in such a way that the pFUS_A plasmid was inserted with HD1, HD2, NG3, NG4, NI5, NG6, NI7, NI8, NN9, and HD10 modules and the pFUS_B5 plasmid was inserted with NI1, HD2, NI3, NG4, and NI5 modules by restriction enzyme BsaI treatment and ligation, respectively. The Wx_TALEN-B2 was constructed by joining in such a way that the pFUS_A plasmid was inserted with NN1, NG2, HD3, NN4, HD5, NG6, NI7, NI8, NI9, and NI10 modules and the pFUS_B8 plasmid was inserted with HD1, NG2, HD3, NI4, NI5, NI6, HD7, and NI8 modules by restriction enzyme BsaI treatment and ligation, respectively. The pZHY500-WxA1 was constructed by joining in such a way that the pZHY500 was inserted with the final module (pLR-NG, half-repeat) of the repeating constructed in the pFUS_A and pFUS_B5 plasmids of Wx_TALEN-A1 by restriction enzyme Esp3I treatment and ligation. The pZHYS01-WxB2 was constructed by joining in such a way that the pZHY501 was inserted with the final module (pLR-NG, half-repeat) of the repeating constructed in the pFUS_A and pFUS_B8 plasmids of Wx_TALEN-B2 by restriction enzyme Esp3I treatment and ligation.

(Example 3) Preparation of TALEN-A/Xcc and TALEN-B/Xcc

Present Example used tobacco and black rot bacteirum (Xcc) as an example of a plant-bacteria combination suitable for introducing a protein into a plant using the type III secretion system.

Regarding a protein expression promoter in bacterial cells and a signal sequence to be recognized by the type III secretion system, a usable promoter is any high expression promoter or a promoter of a gene induced by infection, and the signal sequence and the promoter of Xcc1072 of the type III secretion system (conserved hypothetical protein [*Xanthomonas campestris* pv. *campestris* str. ATCC33913] GenBank: AAM40371.1) were used.

Primers Hind3-XCC1072 51 (SEQ ID NO: 7) and Xcc1072 SpeI SacI (SEQ ID NO: 8) were used to amplify the promoter of Xcc1072 and the signal sequence part in the type III secretion system by the PCR method, followed by cloning of the PCR product into pCR-BluntII-TOPO.

TABLE 2

| Name | Sequence (5' → 3') |
|---|---|
| Hind3-XCC1072 51 | atatAAGCTTgccacagaagtcactgggaagg (SEQ ID NO: 7) |
| Xcc1072 SpeI SacI | cCATACTAGTccaaccacttgcgTCCTTCCAA CTAACctttctcttttttctttggagggggagga agcCATctttgcgagccgggcgcgctcc (SEQ ID NO: 8) |

The sequences of the obtained clones were confirmed, and the clones inserted in the opposite direction as viewed from LacZ were selected, which were excised by cleaving with restriction enzymes HindIII and KpnI and then inserted into pME6031 cleaved with HindIII and KpnI in the same manner. The resultant was the foreign gene transportable expression vector Xcc #5/pME6031 by the type III secretion system. Note that, in addition to the signal sequence and the promoter of Xcc1072, there was a terminal sequence (5'-gcttcctcccctccaaagaaaaagagaaag-3' (SEQ ID NO: 9)) upstream of the XbaI site of the TALEN gene in a manner adjacent to the SpeI site between the restriction enzyme HindIII site and the SpeI site of Xcc #5/pME6031.

After Xcc #5/pME6031 was treated with the restriction enzyme KpnI, the ends were blunted with T4 DNA polymerase, followed by further cleaving with the restriction enzyme SpeI. The resultant was used as a vector. This vector was inserted with the TALEN gene which was obtained as follows. After cleaving with SacI from pZHY500-WxA1 and pZHY501-WxB2 being plasmids carrying the TALEN genes WxA1 and WxB2 that recognize the Wx sequence, the ends were blunted with T4 DNA polymerase, followed by further cleaving with restriction enzyme XbaI. In this way, plasmids for expressing WxA1 TALEN and WxB2 TALEN in bacteria were prepared. The prepared plasmids were allowed to proliferate in E. coli and re-introduced after sequence confirmation into the bacteria to be inoculated in the plant. The introduction into the bacteria was conducted by the electroporation method. Bacteria obtained by transforming these plasmids into Xcc are referred to as "TALEN-A/Xcc" and "TALEN-B/Xcc," respectively.

The inoculation of bacteria into the plant was conducted by infiltration using a syringe (needleless syringe). The suspension for inoculation used was a 10 mM MgCl2 solution. The inoculation concentration was a concentration around O.D. 600=0.05, 70% ethanol and sodium hypochlorite were used for surface sterilization of bacteria, and an antibiotic (rifampicin) was used for Xcc elimination.

(Example 4) Method for Producing Genome Edited Plant (1) Infiltration

Figure 2A:
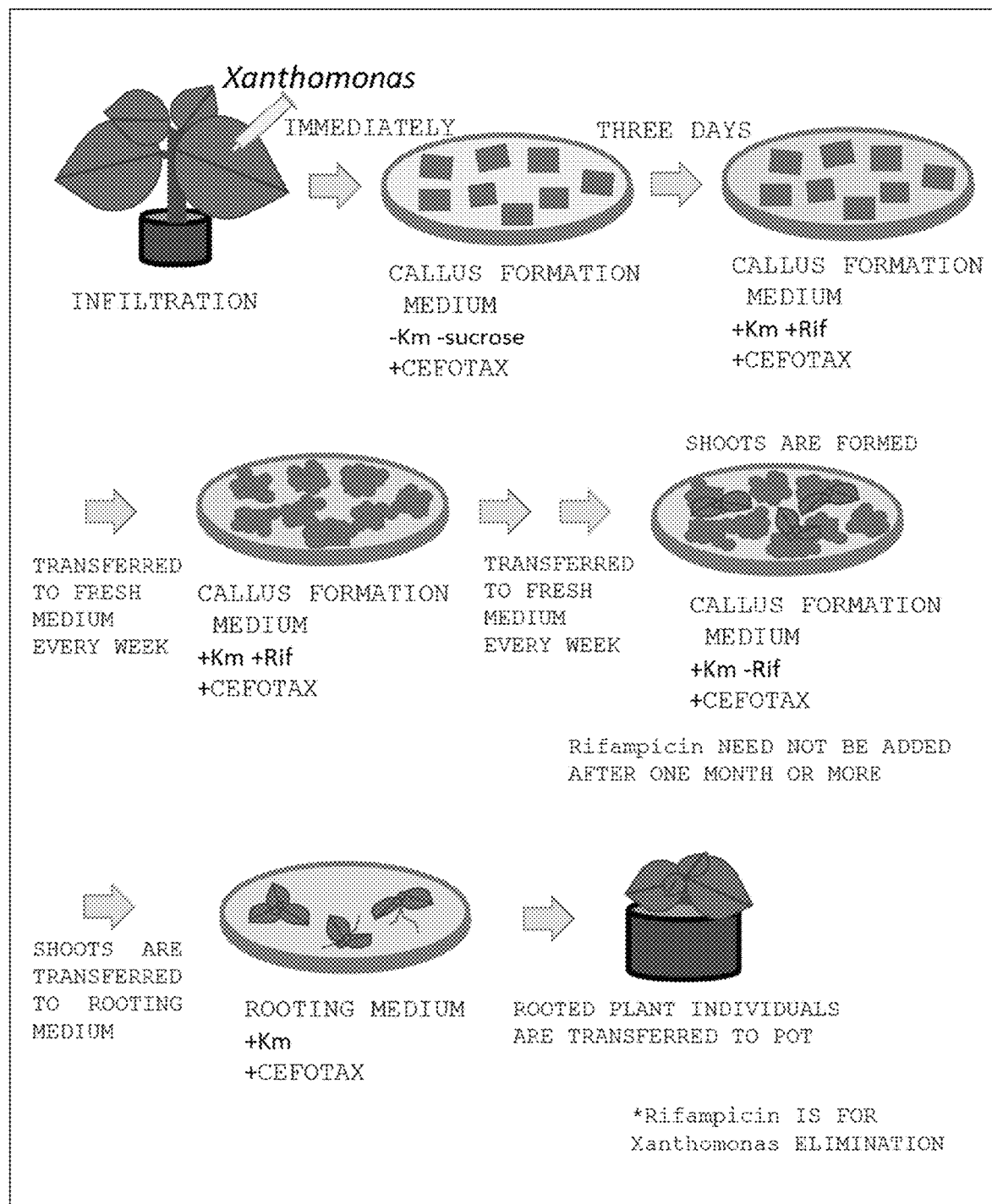
FIG. 2A is a schematic diagram illustrating a method (example) of producing a genome edited plant in the present invention.

FIG. 2A illustrates an overview of the method for producing a genome edited plant. First, TALEN-A/Xcc and TALEN-B/Xcc were each cultured overnight in an LB liquid medium such that the OD600 was 0.5 to 1.0. Each of them was centrifuged at 3,000 rpm to collect the precipitates, followed by resuspension with 1 ml of 10 mM $MgCl_2$. The resultant was further centrifuged at 3,000 rpm to collect the precipitates, followed by resuspension with 10 mM MgCl2 such that OD600=0.05. The solutions of TALEN-A/Xcc and TALEN-B/Xcc were mixed in equal amounts, and the mixture was infiltrated with a syringe into the sGFP-wTALEN-ELUC plant. As a negative control, Xcc having an empty vector (pME6031) was similarly infiltrated.

(2) Tissue Culture Under Bacteriostatic Conditions

After immediate surface sterilization of the infiltrated leaves with 70% ethanol and 1% sodium hypochlorite, the Xcc inoculation portions were cut into 0.5 to 1 cm squares. The cut pieces were arranged on a callus • regeneration induction medium basically using MS medium without the addition of sucrose but with the addition of Cefotax [1× Murashige and Skoog (MS), 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of α-naphthaleneacetic acid, 1 µg/ml of 6-benzylaminopurine, 200 µg/ml of Cefotax, 8.5 g/L of agar, and pH of 5.8] and placed at 28° C. for three days with 16-hour light period/8-hour dark period (bacteriostatic culture).

(3) Tissue Culture and Plant Regeneration Under Bactericidal Conditions

Three days later, the leaves were transferred to a callus formation medium containing 50 µg/ml of rifampicin and 100 µg/ml of kanamycin, and transferred to a fresh medium every week. Note that the medium used was a callus • regeneration induction medium containing rifampicin until one month later, and was thereafter a callus • regeneration induction medium not containing rifampicin but kanamycin. The individuals having shoots formed thereon were transferred to a rooting medium containing 100 µg/ml of kanamycin [1×MS, 1×MS vitamin, 30 g/L of sucrose, 200 µg/ml of Cefotax, 8.5 g/L of agar, and pH of 5.8]. The rooted individuals were transferred to a pot containing vermiculite and grown at 25° C. for 16-hour light period/8-hour dark period.

Figure 2B:
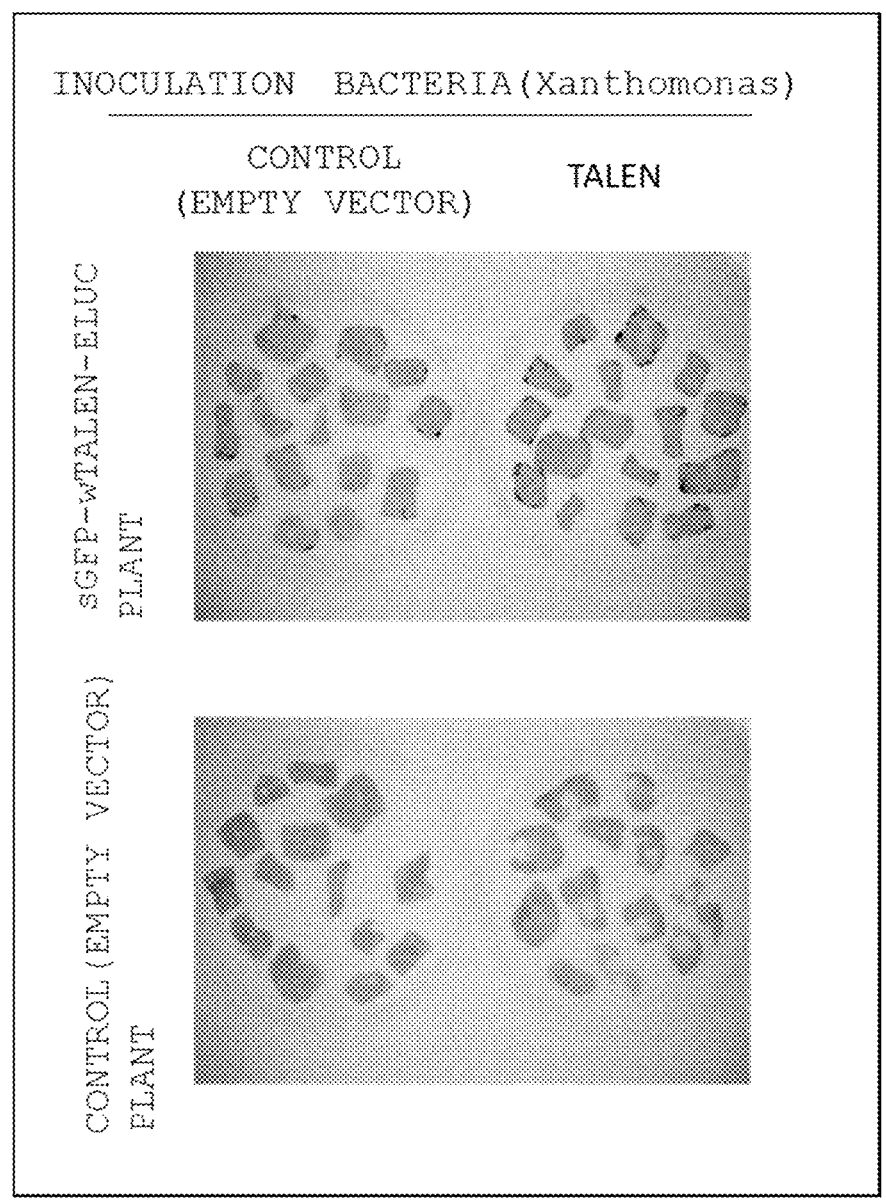
FIG. 2B Tobacco into which the vector of in FIG. 1 was introduced was inoculated with TALEN-expressing black rot bacteirum (Xcc), and the leaf pieces thereof were cultured in a medium added with an antibiotic at a bacteriostatic concentration (200 µg/ml of Cefotax) with limitation on the carbon source (sucrose).
Figure 2C:
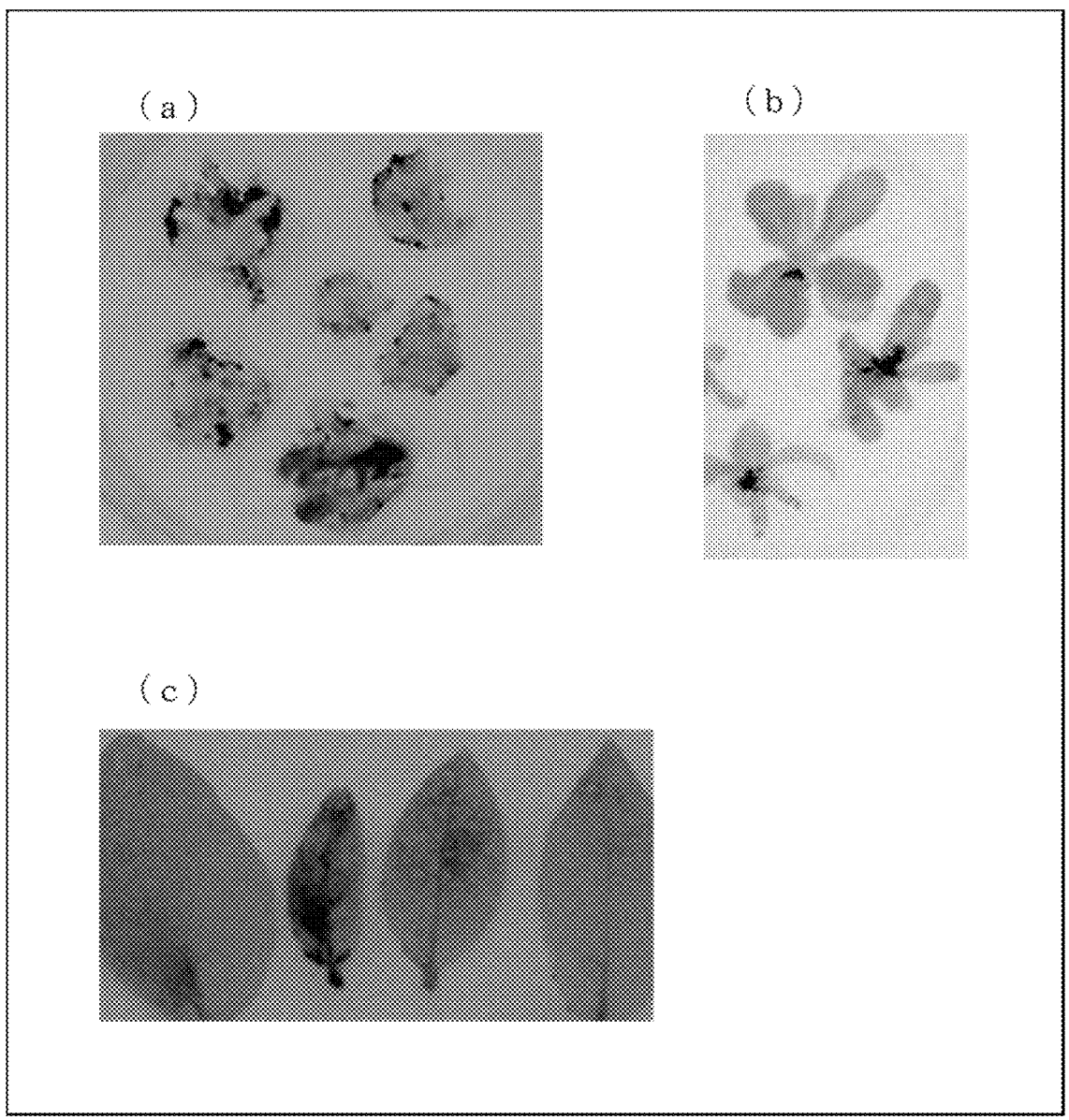
FIG. 2C Tobacco into which the vector of in FIG. 1 was introduced was inoculated with TALEN-expressing black rot bacteirum (Xcc), and the leaf pieces thereof were cultured for three days in a medium added with an antibiotic at a bacteriostatic concentration (200 µg/ml of Cefotax) with limitation on the carbon source (sucrose), followed by transfer to a medium without limitation on the carbon source (containing kanamycin as an antibiotic).

Genome edited individuals were selected using luciferase activity as an index. Specifically, a sodium phosphate buffer containing 1 mM luciferin (pH of 7.0) was sprayed on the leaves to observe luciferase activity with LAS-3000 (FIGS. 2B and 2C).

In addition, it was demonstrated that genome edited individuals were obtained in the same manner in the case of using a callus • regeneration induction medium [1×MS, 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of α-naphthaleneacetic acid, 1 µg/ml of 6-benzylaminopurine, 200 µg/ml of Cefotax, 30 g/L of sucrose, 8.5 g/L of agar, and pH of 5.8] or [1×MS, 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of α-naphthaleneacetic acid, 1 µg/ml of 6-benzylaminopurine, 8.5 g/L of agar, and pH of 5.8] as a medium for bacteriostatic culture in Present Example.

Note that, in the case of infection with bacteria directly followed by culture without undergoing co-culture under bacteriostatic conditions, the efficiency of mutation introduction was poor (that is, the portions where luminescence was detected were small in size and number), and the following acquisition of luminescent regeneration individuals was not successful.

Figure 3:
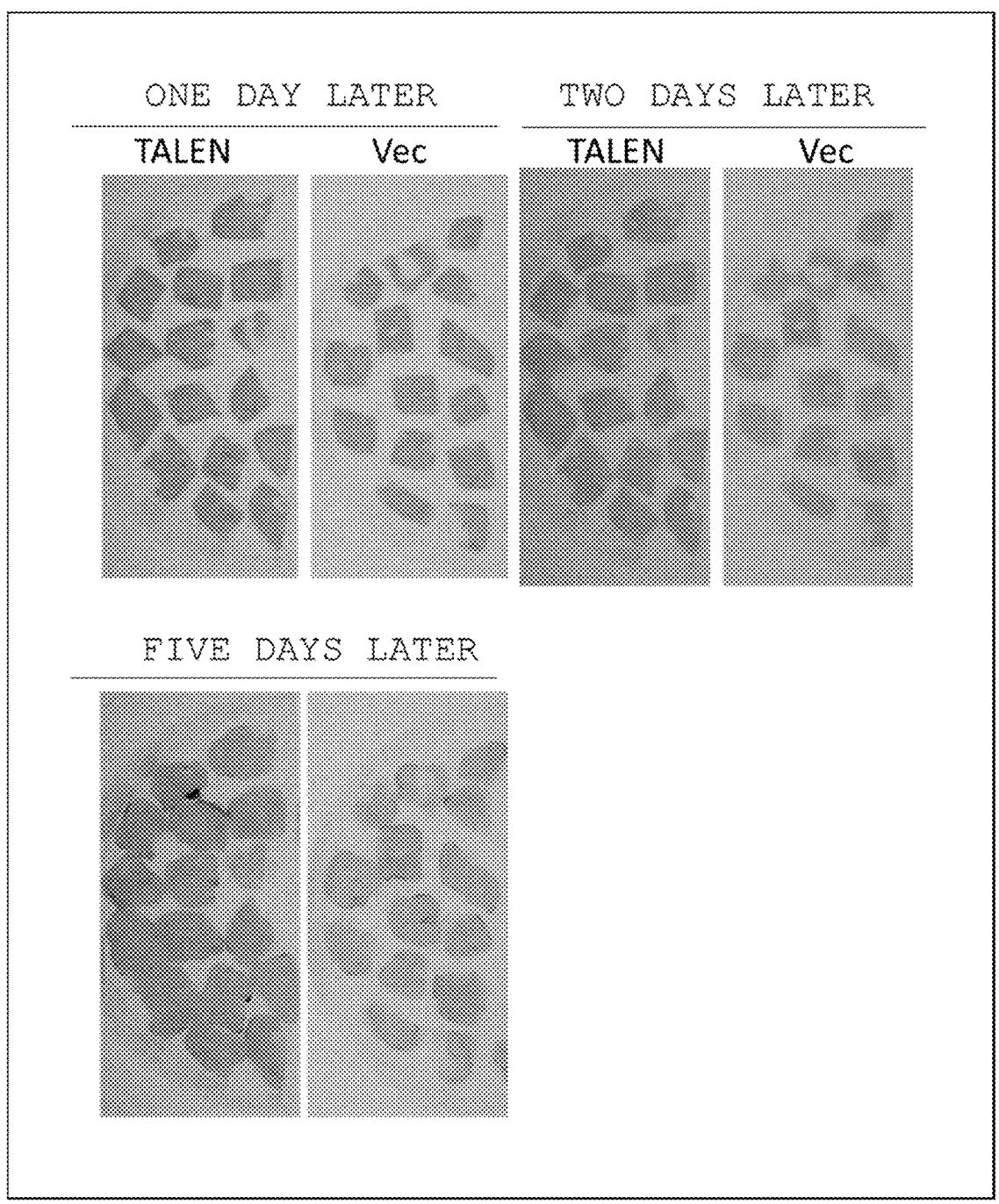
FIG. 3 Tobacco into which the vector of in FIG. 1 was introduced was inoculated with TALEN-expressing black rot bacteirum (Xcc), and the leaf pieces thereof were cultured in a medium added with an antibiotic at a bacteriostatic concentration (30 g/L of sucrose, 200 µg/ml of Cefotax) without limitation on the carbon source (sucrose).

(4) Verification Under Various Tissue Culturing Conditions (a) As a medium for tissue culture under bacteriostatic conditions, a callus • regeneration induction medium basically using MS medium with the addition of sucrose and Cefotax [1× Murashige and Skoog (MS), 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of α-naphthaleneacetic acid, 1 µg/ml of 6-benzylaminopurine, 30 g/L of sucrose, 200 µg/ml of Cefotax, 8.5 g/L of agar, and pH of 5.8] was used to conduct an experiment in the same manner as described above, followed by detection of the occurrence of genome editing on the leaf pieces for various culturing periods (one day, two days, and five days after culture) using luciferase activity as an index. As a result, genome editing by TALEN was observed any of one day, two days, and five days after culture (FIG. 3).

Figure 4:
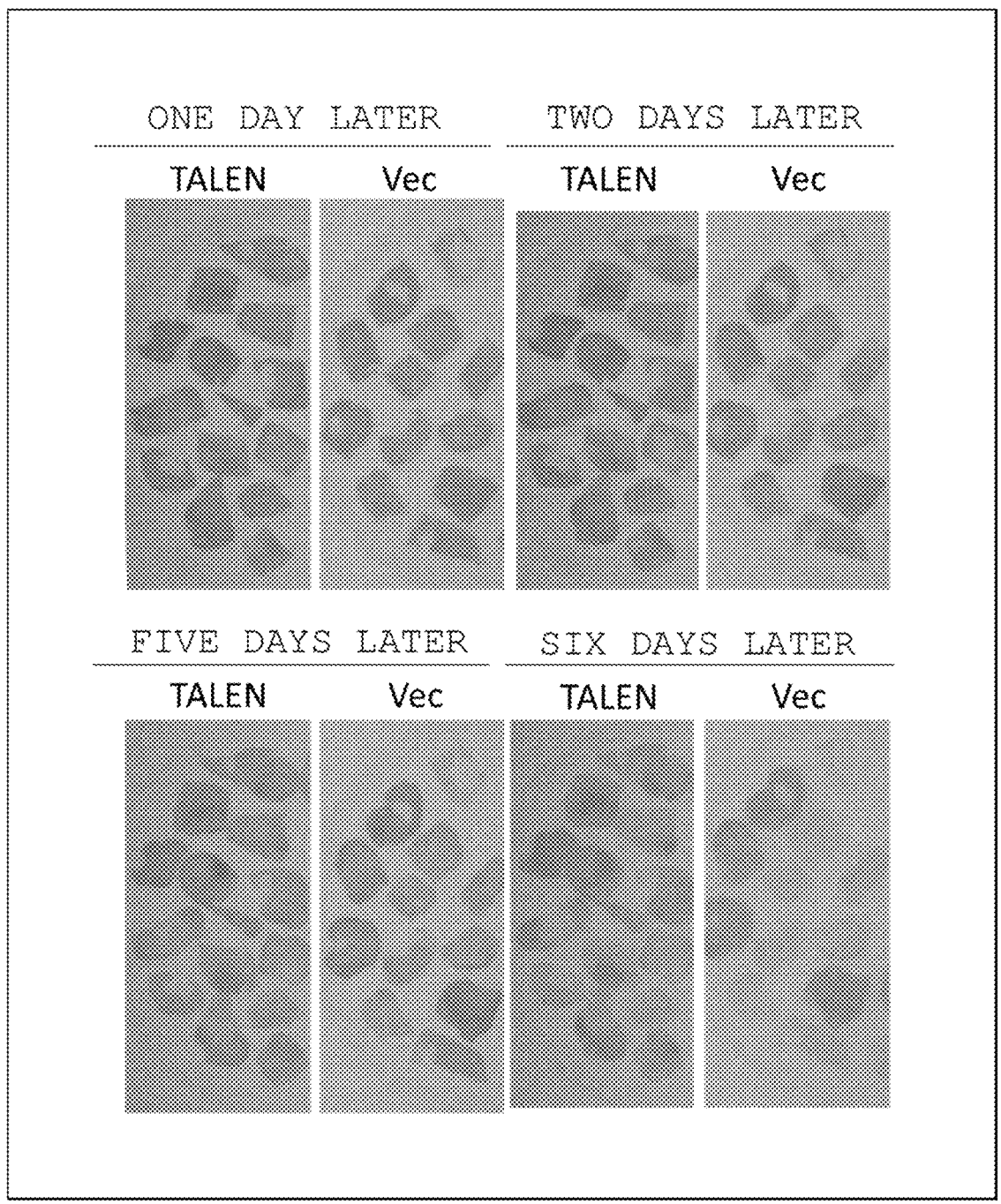
FIG. 4 Tobacco into which the vector of in FIG. 1 was introduced was inoculated with TALEN-expressing black rot bacteirum (Xcc), and the leaf pieces thereof were cultured in a medium added with an antibiotic at a bacteriostatic concentration (200 µg/ml of Cefotax) with limitation on the carbon source (sucrose).

(b) As a medium for tissue culture under bacteriostatic conditions, a callus • regeneration induction medium basically using MS medium without the addition of sucrose but with the addition of Cefotax [1× Murashige and Skoog (MS), 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of Ω-naphthaleneacetic acid, 1 µg/ml of 6-benzylaminopurine, 200 µg/ml of Cefotax, 8.5 g/L of agar, and pH of 5.8] was used to conduct an experiment in the same manner as described above, followed by detection of the occurrence of genome editing on the leaf pieces for various culturing periods (one day, two days, five days, and six days after culture) using luciferase activity as an index. As a result, genome editing by TALEN was observed one day and two days after culture but was not observed five days and six days later (FIG. 4). The leaves had begun to die six days later. In consideration of the results in FIG. 2B (3 days after culture) together, it was found that the period of bacteriostatic culture in a medium not containing sucrose is preferably less than 5 days.

Figure 5:
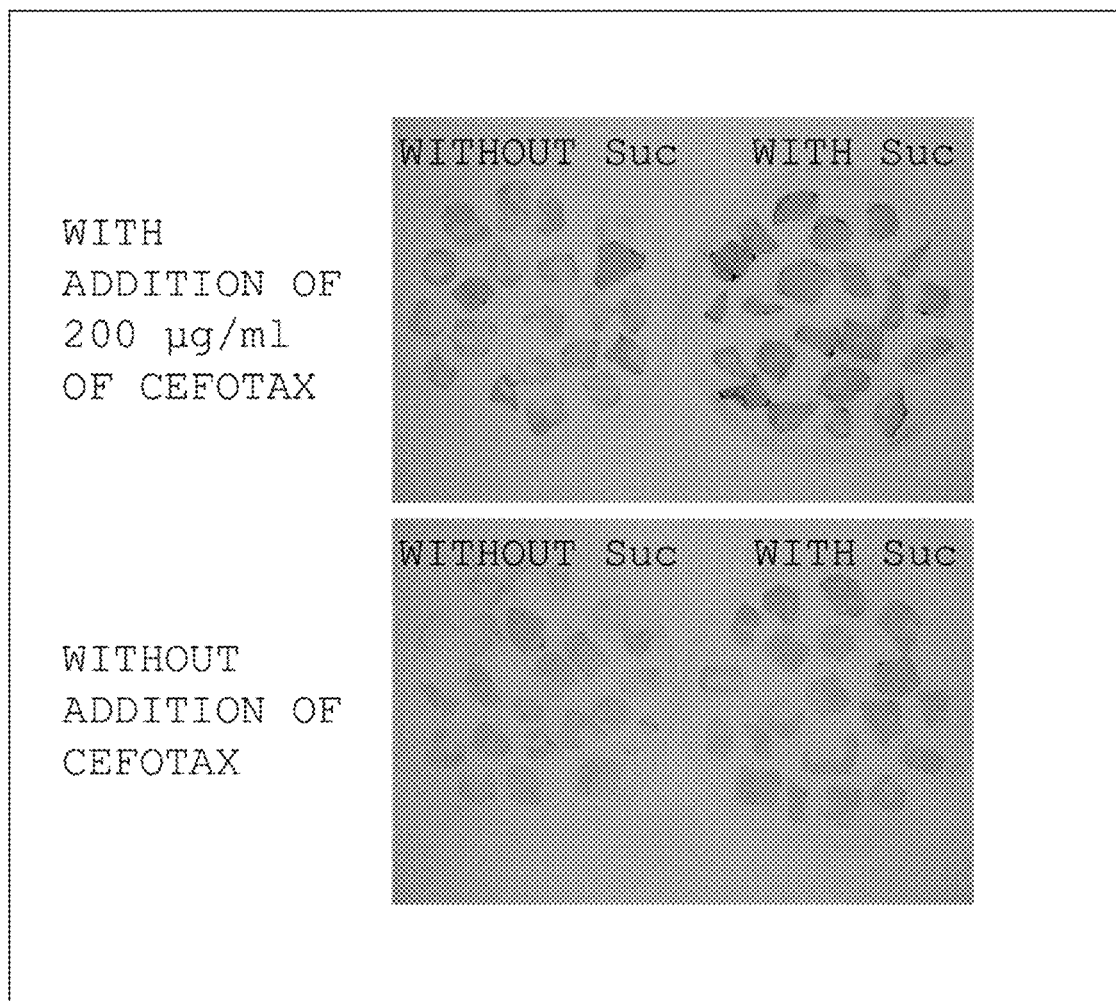
FIG. 5 Tobacco into which the vector of in FIG. 1 was introduced was inoculated with TALEN-expressing black rot bacteirum (Xcc), and the leaf pieces thereof were cultured in media with various conditions (with or without the addition of 30 g/L of sucrose and with or without the addition of 200 µg/ml of Cefotax).

(c) As a medium for tissue culture under bacteriostatic conditions, a callus • regeneration induction medium basically using MS medium with or without the addition of sucrose and Cefotax [1× Murashige and Skoog (MS), 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of α-naphthaleneacetic acid, 1 µg/ml of 6-benzylaminopurine, (with or without the addition of) 30 g/L of sucrose, (with or without the addition of) 200 µg/ml of Cefotax, 8.5 g/L of agar, and pH of 5.8] was used to conduct an experiment in the same manner as described above, followed by detection of the occurrence of genome editing on the leaf pieces three days after culture using luciferase activity as an index. As a result, genome editing by TALEN was observed in the case of adding Cefotax (FIG. 5). In the case of not adding Cefotax, a weak signal was detected under the condition of not adding sucrose either, but no signal was detected under the condition of adding sucrose with damage observed in the leaves (lower part of FIG. 5).

Figure 6:
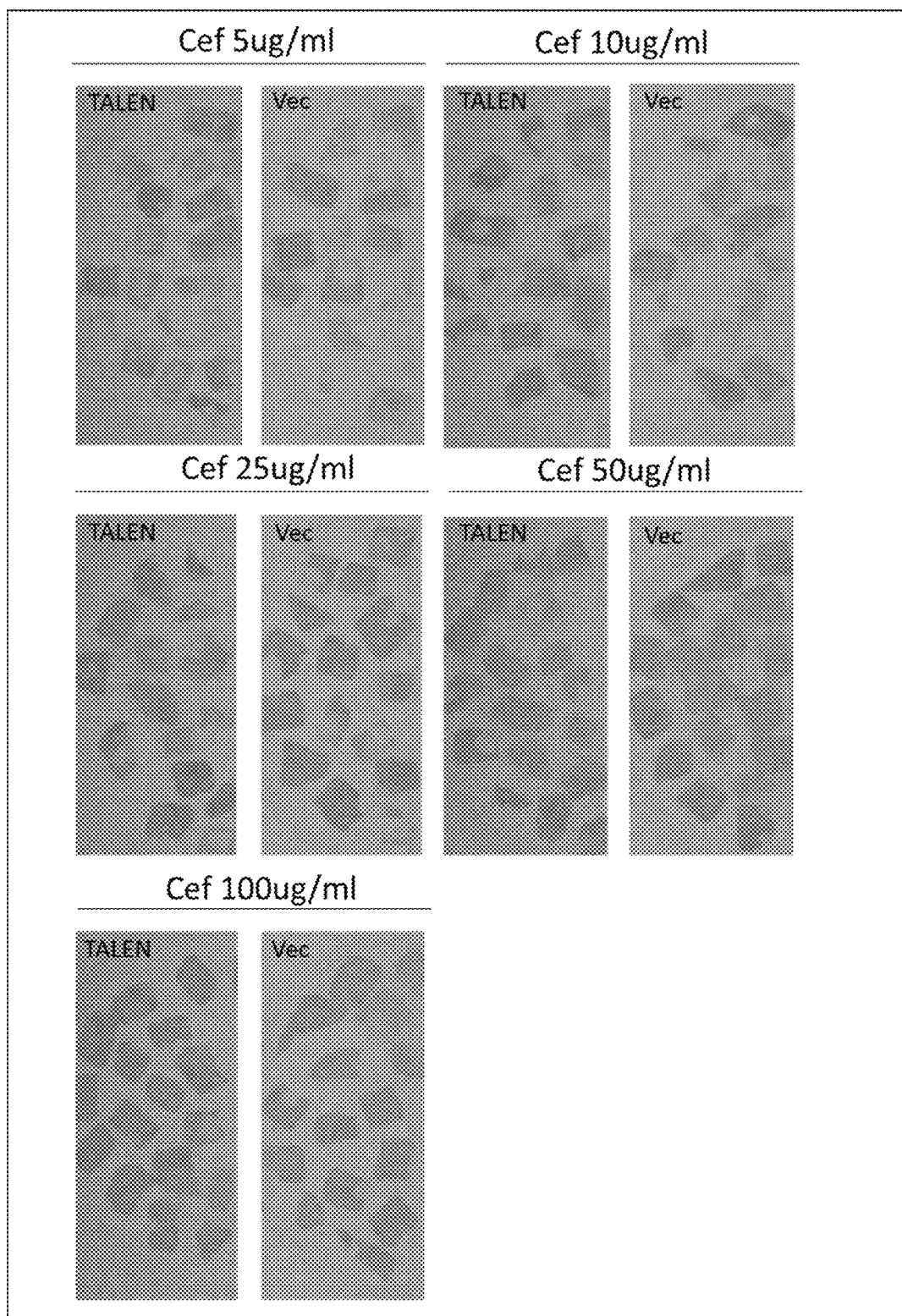
FIG. 6 Tobacco into which the vector of in FIG. 1 was introduced was inoculated with TALEN-expressing black rot bacteirum (Xcc), and the leaf pieces thereof were cultured in media added with various concentrations of antibiotic (5 to 100 µg/ml of Cefotax) with limitation on the carbon source (sucrose).

(d) As a medium for tissue culture under bacteriostatic conditions, a callus • regeneration induction medium basically using MS medium without the addition of sucrose but with the addition of various concentrations of Cefotax [1× Murashige and Skoog (MS), 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of α-naphthaleneacetic acid, 1 µg/ml of 6-benzylaminopurine, Cefotax (5, 10, 25, 50, and 100 µg/ml), 8.5 g/L of agar, and pH of 5.8] was used to conduct an experiment in the same manner as described above, followed by detection of the occurrence of genome editing on the leaf pieces three days after culture using luciferase activity as an index. As a result, genome editing by TALEN was observed in the case of adding 100 µg/ml of Cefotax but was not observed for the other concentrations with damage observed in the leaves (FIG. 6).

(5) Selection of Genome Edited Individuals Using Drug Resistant Gene

Figure 7:
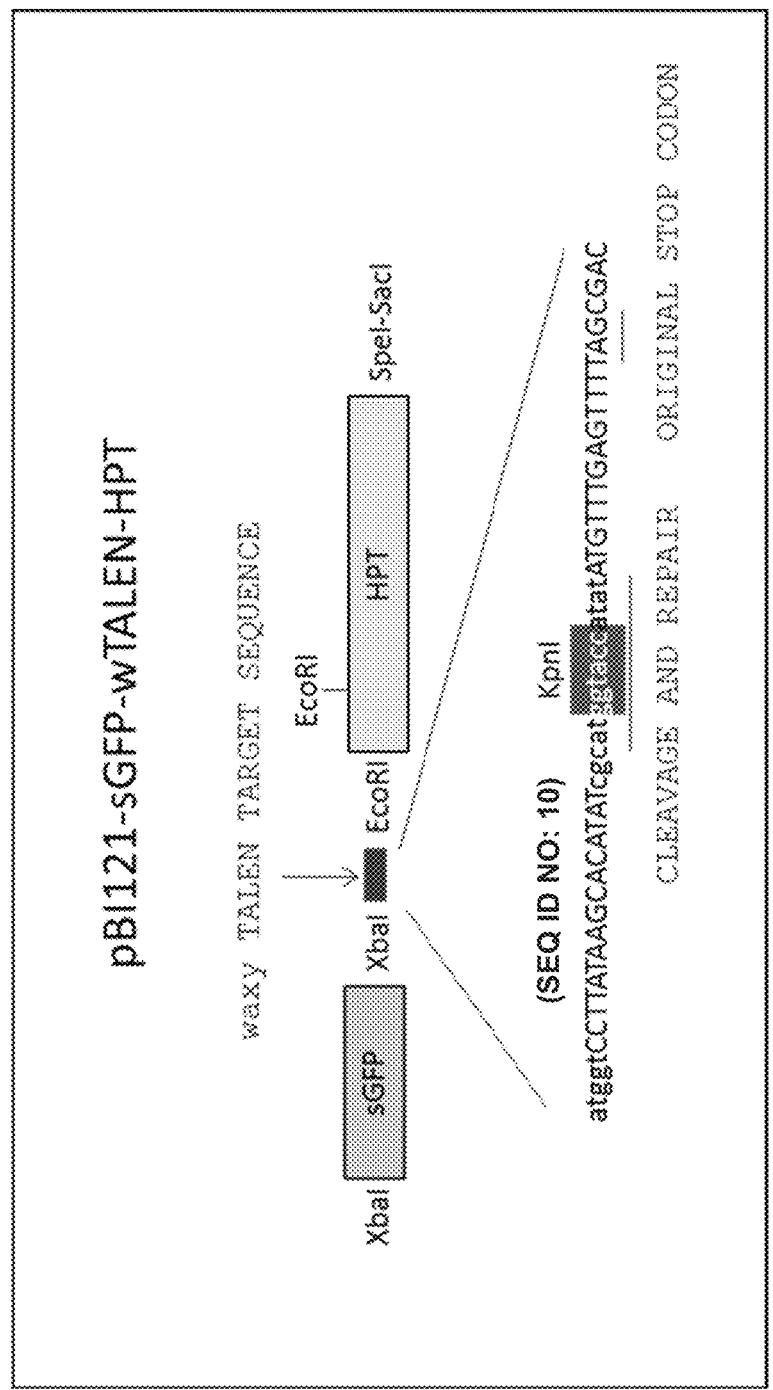
FIG. 7 is a diagram illustrating the vector "pBI121-sGFP-wTALEN-HPT" used in Present Examples.
Figure 8A:
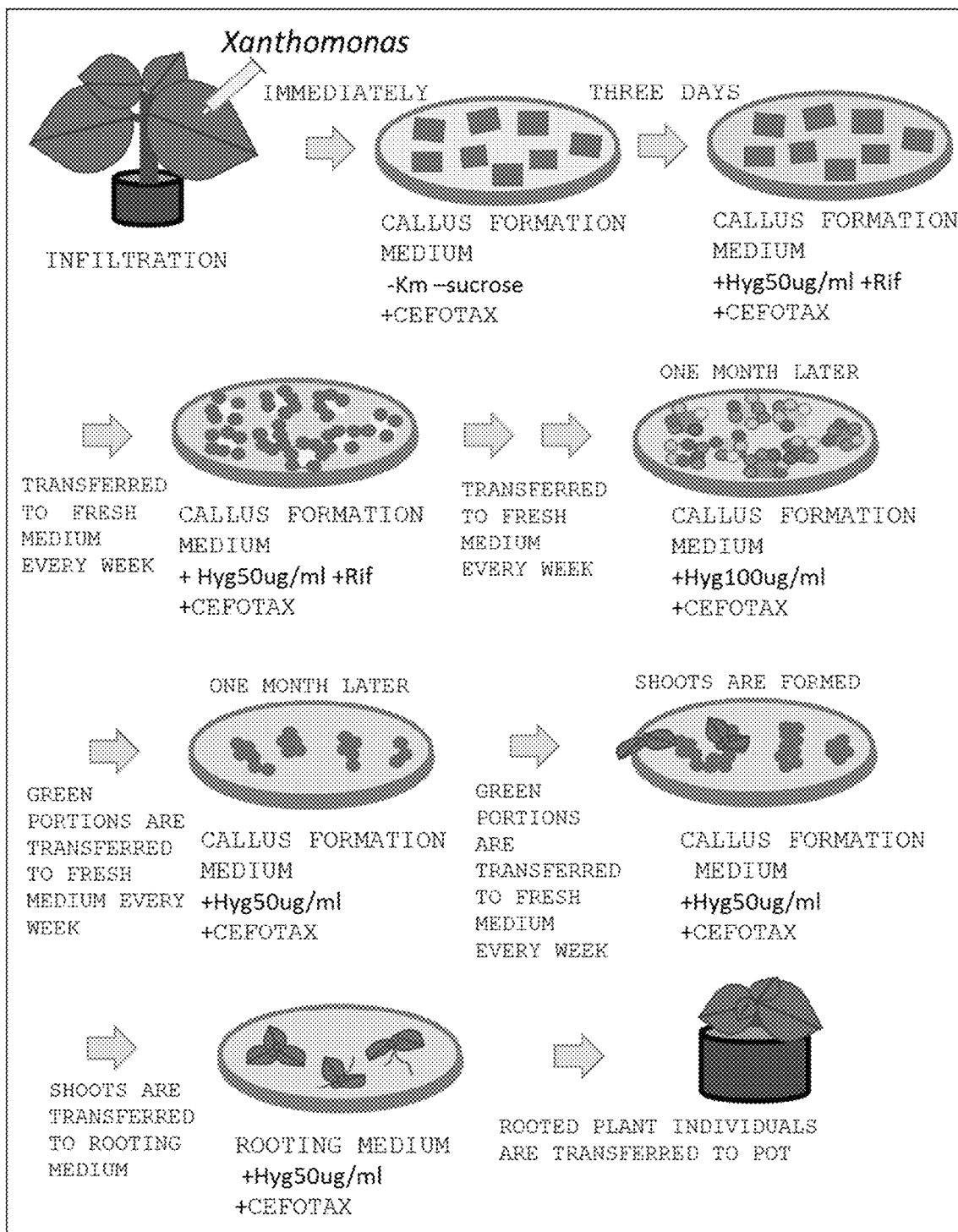
FIG. 8A is a schematic diagram illustrating a method (example) of producing a genome edited plant in the present invention.
Figure 8B:
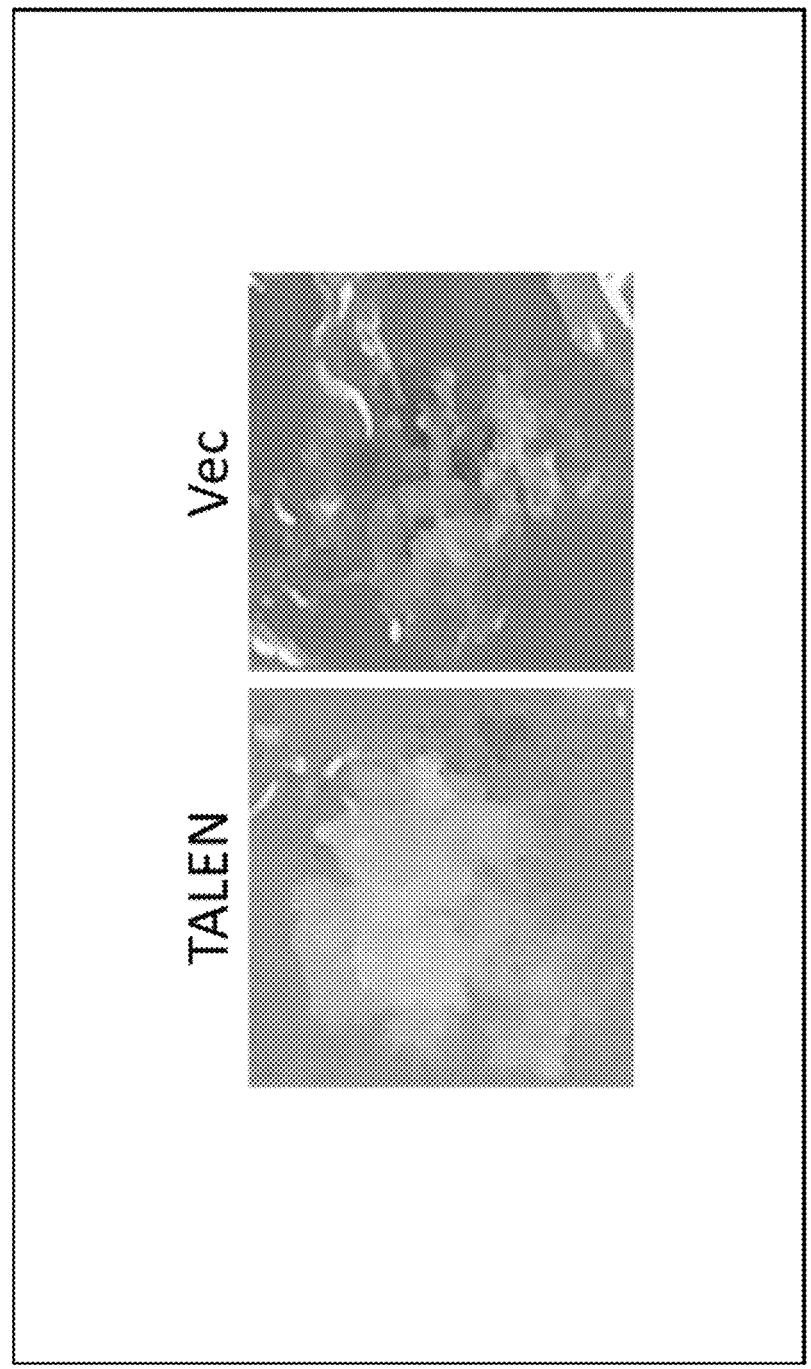
FIG. 8B Tobacco into which the vector of in FIG. 7 was introduced was inoculated with TALEN-expressing black rot bacteirum (Xcc), and the leaf pieces thereof were cultured for three days in a medium added with an antibiotic at a bacteriostatic concentration (200 μg/ml of Cefotax) with limitation on the carbon source (sucrose), followed by transfer to a medium without limitation on the carbon source (containing hygromycin as an antibiotic).

For the purpose of selecting genome edited individuals using drug resistance as an index, a vector "pBI121-sGFP-wTALEN-HPT" was constructed in which the luciferase gene (ELUC) of pBI121-sGFP-wTALEN-ELUC (FIG. 1) was replaced with the hygromycin resistance gene (HPT) (FIG. 7). This vector was used to produce a genome edited plant (an overview is illustrated in FIG. 8A). Specifically, a sGFP-wTALEN-HPT plant was infiltrated in the same manner as in (1) above. After that, bacteriostatic culture was conducted for three days in the same manner as in (2) above. Tissue culture under bactericidal conditions and regeneration of the plant were conducted in the same manner as in (3) above, except that a medium containing hygromycin as an antibiotic was used. As a result, callus grew in the seventh week after inoculation, which revealed that genome editing had occurred (FIG. 8B). Note that, in the negative control (Vec), the tissue was browned.

(Example 5) Production of Genome Edited Plant Using Meganuclease

The meganuclease T-SceI recognizes an 18-base sequence [5'-TAGGGATAA↓CAGGGTAAT-3']), generates a 4-base overhanging end of 3'-OH, and cleaves even with a 1-base substitution in the recognition sequence. The recognition sequence of meganuclease I-SceI was placed in front of the ELUC sequence (without sGFP), and meganuclease cleavage followed by mutation introduction was conducted to prepare a luminescent construction product. If this is left as it is, translation of ELUC does not occur because a stop codon is made. However, if insertion or deletion occurs in the blue part due to cleavage by I-SceI followed by repair errors, the sequence of the downstream ELUC gene is translated so that luminescence with luciferin as a substrate can be observed.

Figure 9:
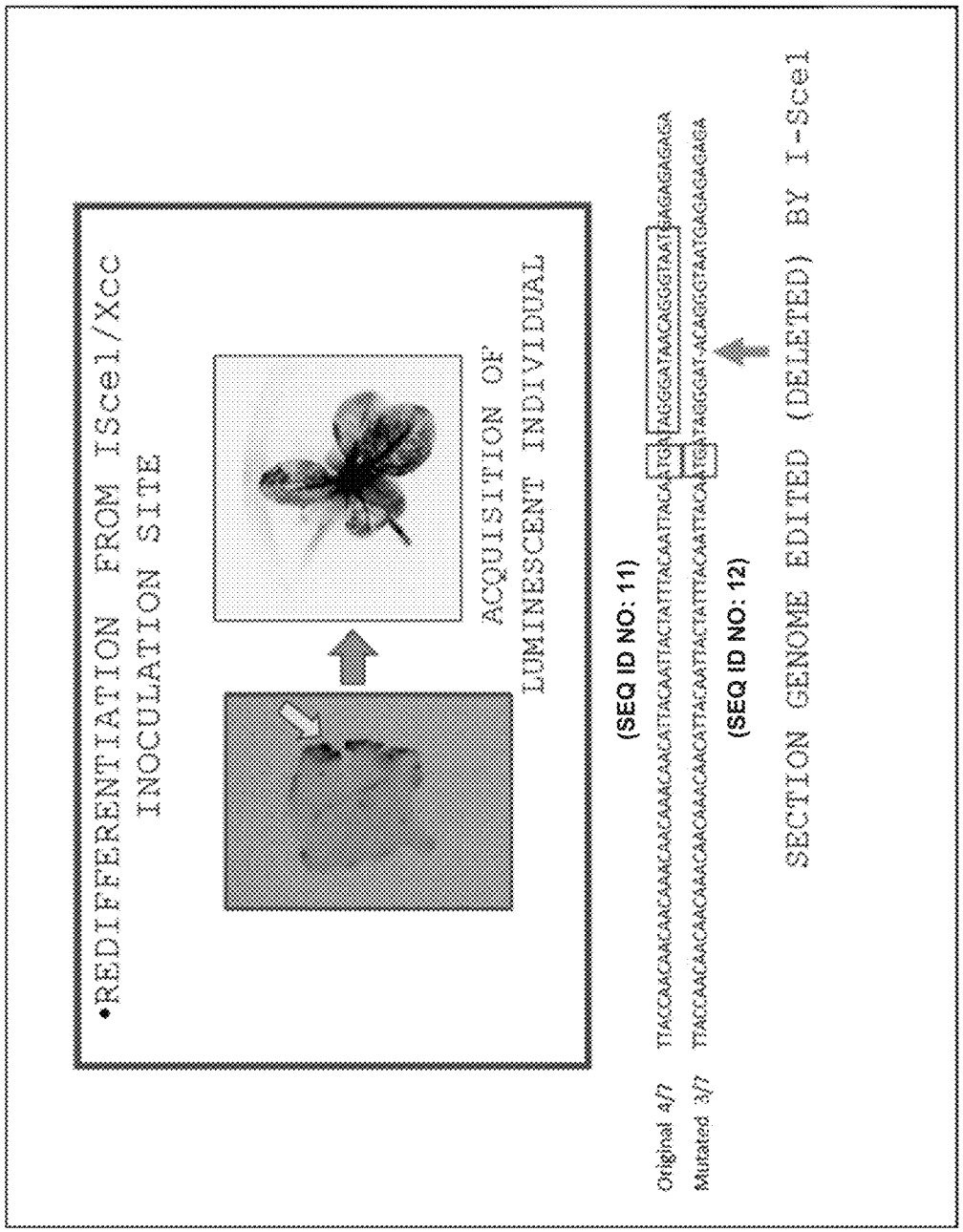
FIG. 9 The same experiment was conducted by inoculating black rot bacteirum (Xcc), expressing I-SceI instead of TALENs as a genome editing molecule, in tobacco into which a vector containing a recognition sequence thereof was introduced.

The I-SceI gene (Jacquiet and Dujon, Cell, 41: 383-394 (1985)) was cloned into a bacterial type III secretion type protein expression vector as described above followed by introduction into Xcc. This I-SceI-expressing Xcc was cultured, collected, and suspended in a 10 mM MgCl2 solution to O.D. 600=0.05, followed by inoculation into a reporter tobacco plant by the infiltration method. Three days after inoculation, luciferin was sprayed to observe luminescence using a CCD camera. After that, the inoculated leaves were cut off, subjected to surface sterilization, and placed on an agar medium prepared by aseptically adding 5 µg/ml of rifampicin to a tobacco regeneration medium [1×MS, 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 0.1 µg/ml of α-naphthaleneacetic acid, 1 µg/ml of 6-benzylaminopurine, 200 µg/ml of Cefotax, 50 µg/ml of kanamycin, 30 g/L of sucrose, 8.5 g/L of agar, and pH of 5.8], followed by regeneration of the shoots. Luciferin was added to the redifferentiated shoots to observe luminescence, followed by repeated selection of shoots with strong luminescence. The obtained shoots were placed on a rooting medium [1×MS, 1×MS vitamin (0.1 µg/ml of thiamine hydrochloride, 0.5 µg/ml of pyridoxine hydrochloride, 0.5 µg/ml of nicotinamide, 2 µg/ml of glycine, and 100 µg/ml of myo-inositol), 200 µg/ml of Cefotax, 50 µg/ml of kanamycin, 30 g/L of sucrose, 8.5 g/L of agar, and pH of 5.8] for regeneration as individuals. As a result of extracting DNA from the regenerated individuals and analyzing the sequence, a 1-base deletion capable of restoring the expression of ELUC gene was observed (FIG. 9).

INDUSTRIAL APPLICABILITY

As described above, the present invention makes it possible to efficiently produce a plant into which the protein of interest has been introduced. Since the method of the present invention does not incorporate a gene into a plant genome, a plant obtained in this way is also excellent in terms of safety as food and environment (biodiversity) in the case of cultivation in the outside, for example. Therefore, the present invention can widely contribute to the field of agriculture and the like.

[Sequence Listing]

The invention claimed is:

1. A method for producing a plant into which a desired protein is introduced, the method comprising the steps of (a) to (d):
   (a) preparing transformed bacteria by introducing DNA encoding a desired protein into a bacteria having a type III secretion system;
   (b) bringing the transformed bacteria into contact with a plant;
   (c) transferring a tissue of the plant infected with the transformed bacteria to a medium, followed by culture under a condition that the transformed bacteria are suppressed from proliferating but not killed; and
   (d) redifferentiating the tissue of the plant by performing culture under a condition that the transformed bacteria are killed, wherein the DNA encoding the desired protein is not incorporated into the plant genome in the redifferentiated plant tissue.

2. The method according to claim 1, wherein the culturing condition of the step (c) is at least one of limitation on a nutrient source and addition of an antibiotic.

3. The method according to claim 1, wherein a period of the culture of the step (c) is one to ten days.

* * * * *

SEQUENCE LISTING

<160> NUMBER OF SEQ ID NOS: 12

<210> SEQ ID NO 1
<211> LENGTH: 61
<212> TYPE: DNA

<213> ORGANISM: Artificial Sequence
<220> FEATURE:
<223> OTHER INFORMATION: Synthetic sequence, XbaI-wTALEN-EcoRI-F

<400> SEQUENCE: 1
ctagaatggt ccttataagc acatatcgca tggtaccata tatgtttgag ttttagcgac    60
g                                                                   61

<210> SEQ ID NO 2
<211> LENGTH: 61
<212> TYPE: DNA
<213> ORGANISM: Artificial Sequence
<220> FEATURE:
<223> OTHER INFORMATION: Synthetic sequence, EcoRI-wTALEN-XbaI-R

<400> SEQUENCE: 2
aattcgtcgc taaaactcaa acatatatgg taccatgcga tatgtgctta taaggaccat    60
t                                                                   61

<210> SEQ ID NO 3
<211> LENGTH: 28
<212> TYPE: DNA
<213> ORGANISM: Artificial Sequence
<220> FEATURE:
<223> OTHER INFORMATION: Synthetic sequence, EcoRI-ELUC-F

<400> SEQUENCE: 3
tgaattcatg gagagagaga agaacgtg                                       28

<210> SEQ ID NO 4
<211> LENGTH: 29
<212> TYPE: DNA
<213> ORGANISM: Artificial Sequence
<220> FEATURE:
<223> OTHER INFORMATION: Synthetic sequence, SpeI-ELUC-R

<400> SEQUENCE: 4
tactagttta cagcttagaa gccttctcc                                      29

<210> SEQ ID NO 5
<211> LENGTH: 27
<212> TYPE: DNA
<213> ORGANISM: Artificial Sequence
<220> FEATURE:
<223> OTHER INFORMATION: Synthetic sequence, XbaI-sGFP-F

<400> SEQUENCE: 5
agtctagaat ggtgagcaag ggcgagg                                        27

<210> SEQ ID NO 6
<211> LENGTH: 28
<212> TYPE: DNA
<213> ORGANISM: Artificial Sequence
<220> FEATURE:
<223> OTHER INFORMATION: Synthetic sequence, XbaI-sGFP-R

<400> SEQUENCE: 6
agtctagact tgtacagctc gtccatgc                                       28

<210> SEQ ID NO 7
<211> LENGTH: 32
<212> TYPE: DNA
<213> ORGANISM: Artificial Sequence
<220> FEATURE:
<223> OTHER INFORMATION: Synthetic sequence, Hind3-XCC1072 51

<400> SEQUENCE: 7
atataagctt gccacagaag tcactgggaa gg                                          32

<210> SEQ ID NO 8
<211> LENGTH: 92
<212> TYPE: DNA
<213> ORGANISM: Artificial Sequence
<220> FEATURE:
<223> OTHER INFORMATION: Synthetic sequence, Xcc1072 SpeI SacI

<400> SEQUENCE: 8
ccatactagt ccaaccactt gcgtccttcc aactaacctt tctctttttc tttggagggg            60
aggaagccat ctttgcgagc cgggcgcgct cc                                          92

<210> SEQ ID NO 9
<211> LENGTH: 30
<212> TYPE: DNA
<213> ORGANISM: Artificial Sequence
<220> FEATURE:
<223> OTHER INFORMATION: Synthetic sequence, terminal sequence of TALEN
      gene

<400> SEQUENCE: 9
gcttcctccc ctccaaagaa aaagagaaag                                             30

<210> SEQ ID NO 10
<211> LENGTH: 55
<212> TYPE: DNA
<213> ORGANISM: Artificial Sequence
<220> FEATURE:
<223> OTHER INFORMATION: Synthetic sequence

<400> SEQUENCE: 10
atggtcctta taagcacata tcgcatggta ccatatatgt ttgagtttta gcgac                 55

<210> SEQ ID NO 11
<211> LENGTH: 85
<212> TYPE: DNA
<213> ORGANISM: Artificial Sequence
<220> FEATURE:
<223> OTHER INFORMATION: Synthetic sequence

<400> SEQUENCE: 11
ttaccaacaa caacaaacaa caaacaacat tacaattact atttacaatt acaatgatag            60
ggataacagg gtaatgagag agaga                                                  85

<210> SEQ ID NO 12
<211> LENGTH: 84
<212> TYPE: DNA
<213> ORGANISM: Artificial Sequence
<220> FEATURE:
<223> OTHER INFORMATION: Synthetic sequence

<400> SEQUENCE: 12
ttaccaacaa caacaaacaa caaacaacat tacaattact atttacaatt acaatgatag            60
ggatacaggg taatgagaga gaga                                                   84